US011883114B2

(12) United States Patent
Olafsen et al.

(10) Patent No.: US 11,883,114 B2
(45) Date of Patent: Jan. 30, 2024

(54) ULTRASOUND LOCATABLE SURGICAL GUIDEWIRE SYSTEM AND METHOD

(71) Applicants: Baylor University, Waco, TX (US); Scott & White Healthcare, Temple, TX (US)

(72) Inventors: Linda J. Olafsen, Waco, TX (US); Keith E. Schubert, China Spring, TX (US); Jeffrey S. Olafsen, Waco, TX (US); Samantha Dayawansa, Temple, TX (US); Jason H. Huang, Temple, TX (US)

(73) Assignees: BAYLOR UNIVERSITY, Waco, TX (US); SCOTT & WHITE HEALTHCARE, Temple, TX (US)

( * ) Notice: Subject to any disclaimer, the term of this patent is extended or adjusted under 35 U.S.C. 154(b) by 53 days.

(21) Appl. No.: 17/323,070

(22) Filed: May 18, 2021

(65) Prior Publication Data

US 2021/0353365 A1 Nov. 18, 2021

Related U.S. Application Data

(60) Provisional application No. 63/026,537, filed on May 18, 2020.

(51) Int. Cl.
*A61B 34/20* (2016.01)
*A61B 8/08* (2006.01)

(52) U.S. Cl.
CPC ............ *A61B 34/20* (2016.02); *A61B 8/0841* (2013.01); *A61B 2034/2063* (2016.02)

(58) Field of Classification Search
CPC . A61B 34/20; A61B 8/084; A61B 2034/2063; A61B 2017/22014;

(Continued)

(56) References Cited

U.S. PATENT DOCUMENTS 6,110,121 A * 8/2000 Lenker ................ A61B 8/12
600/463
11,123,141 B2 * 9/2021 Belohlavek ....... A61M 25/0108
(Continued)

FOREIGN PATENT DOCUMENTS

WO 0209587 A2 2/2002
WO 2019066888 A1 4/2019

OTHER PUBLICATIONS

Ikegami et al., Active Vibration Control Using Nitinol and Pizoelectric Ceramics, Journal of Intell. Mater. Syst. And Struct., vol. 1—Apr. 1990; available at https://journals.sagepub.com/doi/pdf/10.1177/1045389X9000100204 (Year: 1990).*
(Continued)

*Primary Examiner* — Yi-Shan Yang
*Assistant Examiner* — Alexei Bykhovski
(74) *Attorney, Agent, or Firm* — Jackson Walker LLP

(57) ABSTRACT

The present disclosure provides a system and method for using widely available ultrasound imaging to overcome the limitations of imaging guidewires and other small objects that may be subwavelength in size relative to an ultrasound wavelength. The system and method can reduce the use of X-rays and exposure to the dangerous effects of radiation and avoids the expense of MRI technology. The subwavelength object, such as a guidewire, can be detected using several methods and associated systems described herein, including the object changing positions at a frequency that creates a brighter ultrasound image of the object as the object progresses across a scanned region of the ultrasound detector. In some embodiments, the movement of the small object causes a different speckle signature than the object itself would otherwise generate. Analysis of changes in speckle patterns due to progressive movement of an object can yield a detectable object.

20 Claims, 6 Drawing Sheets

(58) Field of Classification Search
CPC ..... A61B 8/0841; A61B 8/488; A61B 8/0833; A61B 8/12
See application file for complete search history.

(56) References Cited

U.S. PATENT DOCUMENTS

| | | | |
|---|---|---|---|
| 2007/0066880 A1* | 3/2007 | Lee | A61B 8/12 600/407 |
| 2008/0275380 A1* | 11/2008 | Hennings | A61B 8/12 604/22 |
| 2008/0294037 A1* | 11/2008 | Richter | A61B 8/0833 604/22 |
| 2018/0280005 A1* | 10/2018 | Parmentier | A61B 17/22004 |
| 2020/0268455 A1* | 8/2020 | Zheng | B06B 1/0607 |

OTHER PUBLICATIONS

Ordavo, Ivan, International Search Report for International Patent Application No. PCT/US2021/032891, dated, Aug. 20, 2021.
Ordavo, Ivan, Written Opinion of the International Searching Authority for International Patent Application No. PCT/US2021/032891, dated Aug. 20, 2021.

* cited by examiner

ULTRASOUND LOCATABLE SURGICAL GUIDEWIRE SYSTEM AND METHOD

CROSS REFERENCE TO RELATED APPLICATIONS

This application claims the benefit of U.S. Provisional Application No. 63/026,537, filed May 18, 2020, entitled "Ultrasound Locatable Surgical Guidewire System and Method", which is incorporated herein by reference.

STATEMENT REGARDING FEDERALLY SPONSORED RESEARCH OR DEVELOPMENT

Not applicable.

REFERENCE TO APPENDIX

Not applicable.

BACKGROUND OF THE INVENTION

Field of the Invention

The disclosure generally relates to a system and method with ultrasound technology for locating objects. More specifically, the disclosure relates to a system and method with ultrasound technology especially for locating subwavelength-sized objects.

Description of the Related Art

Tens of millions of people per year undergo some form of neurosurgery. The majority of these surgeries include treatment for traumatic brain injury, stroke, hydrocephalus, and epilepsy, as well as aneurysms and atherosclerotic disease. These surgical procedures often require the use of guidewires and catheters that traverse through the body's complex networks of blood vessels in order to reach diseased areas in the brain. Once a guidewire has reached the desired location, repair of damaged tissues is accomplished through clipping, ablation, and plaque removal. Traversing the guidewire through the body requires continuous imaging to navigate to the lesion and to prevent damaging many of the delicate tissues throughout the body.

Current methods of visualizing guide wires during neurosurgery procedures utilize X-ray-based imaging, fluoroscopy, which can expose the patient to excessive levels of radiation. Exposure is especially concerning during repeated or lengthy procedures. Excessive radiation exposure can lead to acute and long-term side effects on tissues while increasing the risk of several types of cancer. It also requires the use of contrasting imaging agents that can result in life-threatening side effects. Real-time MRI imaging is an emerging alternative for the imaging of guidewires in neurovascular procedures and does not expose the patient to radiation or contrasting agents. While the use of real-time MRI is catching on, it is expensive, increases the overall time of procedure and is not used in complex neurovascular procedures.

Ultrasound has been used to guide needles and catheters in surgery for about 40 years. Ultrasound is a safe (non-ionizing), economic, portable, and widely-available imaging modality. The weaknesses of ultrasound are the poor soft tissue contrast and the impedance of the ultrasound waves by gases and metal or bone. Ultrasound uses high frequency sound typically in the range of 1-10 MHz, with low frequencies (1-3 MHz) used for deeper structures such as the liver or heart, and higher frequencies (5-10 MHz) used for imaging near the skin.

Ultrasound images are generated with a transducer sending an ultrasound pulse into an object, and measuring the resulting returned waves on the same transducer. The returned waves have been reflected, attenuated, scattered, and delayed by the materials and interfaces encountered, and the resulting returned wave carries the information in the magnitudes, delays, phase shifts, and frequency shifts. For instance, the time delay to each returning pulse gives twice the travel time to the surface that reflected the wave. Attenuation specifies the material through which the pulse travels through, which gives the speed of sound allowing distances to be calculated. Typically, a pulse is sent out 30 times per second and the returning waves are measured until the next transmission.

A single transducer creates an image that is initially approximately in a column, which then broadens as it goes deeper into the object (A-mode). When multiple transducers are placed next to each other to produce a 2D image, it is referred to as B-mode.

Ultrasound's resolution is limited by its wavelength, which depends on the frequency of the ultrasound probe and the tissue through which it travels. The resolution limit varies between 500 microns (μm) to 150 microns. Biopsy needles, injection needles, and catheters are easily seen, because they are well above the resolution limit. However, vascular guidewires for neurosurgeries, such as aneurysms, typically have diameters less than 100 microns. Below the resolution limit, targets scatter the sound, creating speckle artifacts. Ultrasound images are riddled with speckle, which reduces the ability to detect low-contrast and/or small-sized targets. Tissue in the human body is composed of numerous structures smaller than an ultrasound wavelength, which is the cause of most of the noise that appears as speckle in ultrasound images. A thin (subwavelength) section of material of an object can create a significant speckle pattern intensity for at least a few pixels, but it may be indistinguishable from the background speckle of the surrounding tissue, particularly near bone. In the case of a non-moving transducer and a non-moving object, the speckle pattern does not change, so the presence of a small subwavelength object could be very hard to distinguish from speckle noise.

Separating the speckle of the small structures from variations in tissue is problematic. Thus, ultrasound has not been the choice for subwavelength object imaging. Other types of intravascular surgery using similarly sized guidewires can suffer similar issues.

Therefore, there is a need to be able to identify small objects, such as guidewires, with ultrasound technology with its reduced health risks compared to X-rays and less expensive than magnetic resonance imaging (MRI) technology.

BRIEF SUMMARY OF THE INVENTION

The present disclosure provides a system and method for using widely available ultrasound imaging to overcome the limitations of imaging guidewires and other small objects that may be subwavelength in size relative to an ultrasound wavelength in relevant media. The system and method can reduce the use of X-rays and exposure to the dangerous effects of radiation and avoids the expense of MRI technology. The subwavelength object, such as a guidewire, can be detected using several methods and associated systems described herein, including the object changing positions at a frequency that creates a brighter ultrasound image of the object from reflected ultrasound waves compared to an ultrasound image at a first state of the object. In some embodiments, the movement of the small object causes a different speckle signature than the object itself would otherwise generate. In other embodiments, an analysis of changes in speckle patterns due to progressive movement of a fixed shape of an object can yield a detectable object. Thus, the dynamic speckle from the moving object can be recognized and used to locate the object within the surrounding tissues or other media.

The disclosure provides a system for detecting objects with ultrasound imaging technology that images by producing ultrasound waves from an ultrasound system, the ultrasound waves having a frequency with a corresponding ultrasound wavelength, comprising an object having a first state at a first state position that is configured to be exposed to a wavefront of the ultrasound waves and a second state by movement of the object to a second state position that is different than the first state position, wherein the ultrasound waves reflect from the first state position and the second state position to create an ultrasound image of the object at the second state that is brighter than an ultrasound image of the object at the first state.

The disclosure also provides a method of detecting an object using ultrasound imaging technology that images by producing from an ultrasound system an ultrasound wave having a frequency with a corresponding ultrasound wavelength, comprising: placing an object capable of at least partially reflecting ultrasound waves into a substance that at least partially conducts ultrasound waves, the object having a first state at a first state position; moving the object to a second state at a second state position that is different than the first state position; allowing ultrasound waves from the ultrasound system to be reflected from the object at the first state position and the second state position; and creating an ultrasound image of the object that is brighter at the second state than an ultrasound image of the object at the first state.

DETAILED DESCRIPTION

Figure 1A:
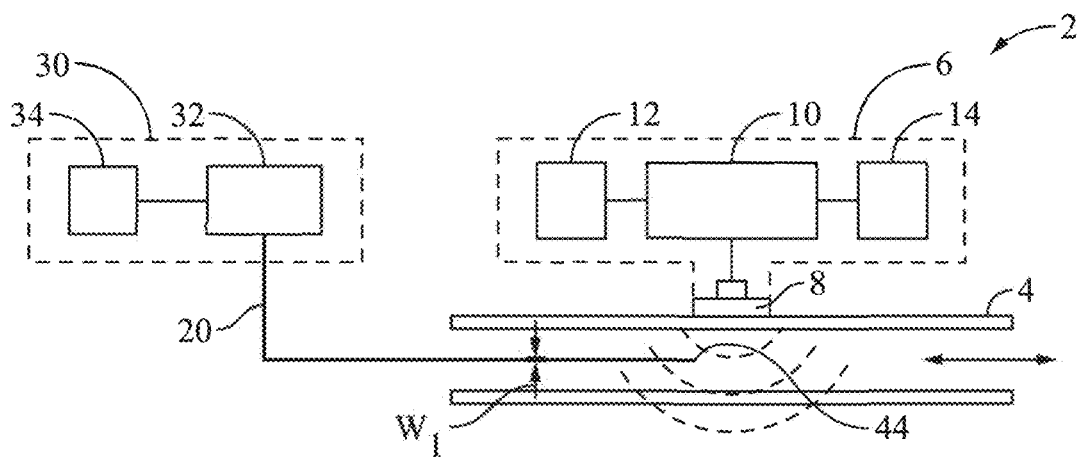
FIG. 1A is a schematic diagram of an embodiment of an ultrasound system with an example of a suitable object to be detected, such as a wire, in a first state.

The Figures described above and the written description of specific structures and functions below are not presented to limit the scope of what Applicant has invented or the scope of the appended claims. Rather, the Figures and written description are provided to teach any person skilled in the art to make and use the inventions for which patent protection is sought. Those skilled in the art will appreciate that not all features of a commercial embodiment of the inventions are described or shown for the sake of clarity and understanding. Persons of skill in this art will also appreciate that the development of an actual commercial embodiment incorporating aspects of the present disclosure will require numerous implementation-specific decisions to achieve the developer's ultimate goal for the commercial embodiment. Such implementation-specific decisions may include, and likely are not limited to, compliance with system-related, business-related, government-related, and other constraints, which may vary by specific implementation or location, or with time. While a developer's efforts might be complex and time-consuming in an absolute sense, such efforts would be, nevertheless, a routine undertaking for those of ordinary skill in this art having benefit of this disclosure. It must be understood that the inventions disclosed and taught herein are susceptible to numerous and various modifications and alternative forms. The use of a singular term, such as, but not limited to, "a," is not intended as limiting of the number of items. Further, the various methods and embodiments of the system can be included in combination with each other to produce variations of the disclosed methods and embodiments. Discussion of singular elements can include plural elements and vice-versa. References to at least one item may include one or more items. Also, various aspects of the embodiments could be used in conjunction with each other to accomplish the understood goals of the disclosure. Unless the context requires otherwise, the term "comprise" or variations such as "comprises" or "comprising," should be understood to imply the inclusion of at least the stated element or step or group of elements or steps or equivalents thereof, and not the exclusion of a greater numerical quantity or any other element or step or group of elements or steps or equivalents thereof. The term "coupled," "coupling," "coupler," and like terms are used broadly herein and may include any method or device for securing, binding, bonding, fastening, attaching, joining, inserting therein, forming thereon or therein, communicating, or otherwise associating, for example, mechanically, magnetically, electrically, chemically, operably, directly or indirectly with intermediate elements, one or more pieces of members together and may further include without limitation integrally forming one functional member with another in a unity fashion. The coupling may occur in any direction, including rotationally. The device or system may be used in a number of directions and orientations. The order of steps can occur in a variety of sequences unless otherwise specifically limited. The various steps described herein can be combined with other steps, interlineated with the stated steps, and/or split into multiple steps. Some elements are nominated by a device name for simplicity and would be understood to include a system or a section, such as a controller would encompass a processor and a system of related components that are known to those with ordinary skill in the art and may not be specifically described. Various examples are provided in the description and figures that perform various functions and are non-limiting in shape, size, description, but serve as illustrative structures that can be varied as would be known to one with ordinary skill in the art given the teachings contained herein. Such examples are sometimes referred to in an adjectival use with the term "exemplary" as a nonlimiting example. The term "subwavelength" means a dimension herein used to indicate a cross sectional length that is normal to a wavefront of an ultrasound wave pulse, and such length is smaller than an ultrasound wavelength in the medium in which the object may be placed for detection. For example, and without limitation, a round subwavelength guidewire would have a diameter as a cross sectional dimension (not a longitudinal length of the guidewire) that is smaller than an ultrasound wavelength in the medium in which the object may be placed for detection. A flat subwavelength guidewire would have a width with a cross sectional dimension in a normal direction that is exposed to a wavefront of an ultrasound wave pulse smaller than an ultrasound wavelength in the medium in which the guidewire may be placed for detection.

The present disclosure provides a system and method for using widely available ultrasound imaging to overcome the limitations of imaging guidewires and other small objects that may be subwavelength in size relative to an ultrasound wavelength in relevant media. The system and method can reduce the use of X-rays and exposure to the dangerous effects of radiation and avoids the expense of MRI technology. The subwavelength object, such as a guidewire, can be detected using several methods and associated systems described herein, including the object changing positions at a frequency that creates a brighter ultrasound image of the object at a second state from reflected ultrasound waves compared to an ultrasound image at a first state of the object. In some embodiments, the movement of the small object causes a dynamic speckle signature than the object itself would otherwise generate. In other embodiments, an analysis of changes in speckle patterns due to progressive movement of a fixed shape of an object can yield a detectable object. Thus, the dynamic speckle from the moving object can be recognized and used to locate the object within the surrounding tissues or other media.

In at least one aspect, the system and method can characterize a speckle variation from a moving object (laterally and/or longitudinally to an intended travel path) and apply a filter designed or trained to separate the speckle patterns induced by movement compared to surrounding background speckle and locate the object. Further, forward movement of a subwavelength object with a distinctly different speed of sound from the surrounding media, can cause a strong speckle scattering, and reduced signal strength on the far side of the object from the source and detector. The speckle from object translational movement is distinct from speckle from object lateral movement. By characterizing the speckle of the object translational movement, some recognition can occur and further in conjunction with speckle of any lateral movement of the object can yield a more accurate analysis of the object. Still further, speckle patterning from different shapes of a given object, such as flat or round, causes different speckle patterns. Different combinations of objects, such as parallel wires compared to twisted wires, can cause different speckle patterns, and can be detected and characterized for recognition.

An example of an object for ultrasound detection is an object having at least one transverse cross section that is subwavelength relative to a wavelength of an ultrasound wave through a medium in which the object may be present. The object can have a length that is equal to or greater than the wavelength of the ultrasound wave. The object can be a wire, such as a guidewire, that can be used in surgical and other medical procedures. A wire is illustrative and shown and described in the Figures as the object with the understanding that the object is not limited to a wire and the teachings herein can be applied to other objects. Therefore, the description and Figures will use and show a wire(s) with the understanding that the principles apply to other objects. Further, the principles herein can apply to objects having a cross section larger than subwavelength. Because such larger objects can be detected with typical ultrasound systems and methods, the invention is particularly helpful for subwavelength object detection although larger objects can benefit from the principles described herein as well.

Ultrasound detection of the guidewire location and a tool and/or payload will reduce radiation exposure from the current technique of continuous X-ray fluoroscopy to guide such objects as catheters inserted by manual means. The system and method can be extremely useful when treating situations where an acute angle or difficult turn is necessary to proceed for treatment. Advantages of the ultrasound system with the ability to detect subwavelength objects can include:

Improved navigation to treatment site,
  Reduced time to reach treatment site, which will increase successful treatment and survival rates in patients,
  Reduced X-ray/ionizing radiation exposure for both patient and physician by employing ultrasound imaging of guidewire,
  Less expensive and more portable, ready access of technology in rural/remote areas, and
  Capability to automate and/or remotely control arterial navigation for treatment in remote locations, such as in battlefields and rural areas.

The subwavelength object can be made of a material having a high value of adiabatic compressibility and density compared to soft tissue to increase the detectability of the object by the ultrasound imaging. For example, a nickeltitanium (nitinol) alloy that is not only elastic but also has the ability for shape memory as a Shape Memory Alloy (SMA), enabling it to undergo deformation at a temperature and then recover to its original shape at another temperature. Generally, energy in the form of a current can be applied to create the temperature(s) that activates the shape deformation. For purposes of this application, an SMA material includes other SMAs in addition to nitinol, shape-memory polymers, and ferromagnetic SMAs. Nitinol material will be used herein in various descriptions of embodiments, but the principles apply to other SMAs and are within the scope of the invention. For example, the object could be a thin guidewire having a subwavelength cross section made of nitinol that is, for example and without limitation, 20 μm, 50 μm, 75 μm, 100 μm, 125 μm, 150 μm, 250 μm or others. The adiabatic compressibility is inversely proportional to the material bulk modulus, which is a standard tabulated value for both soft tissue and metal, so roughly ks≈0.1 k for nitinol to soft tissue. In terms of density, nitinol is about 6.5 times denser than soft tissue. Using these values, the small nitinol wire appears about the same effective size as an object that is seven wavelengths across.

Lateral Motion

Lateral motion in the wire would cause the speckle of the nitinol wire to change, but not the background, resulting in potentially noticeable "flickering" pixels in a highly confined area. In at least some embodiments, motion can be induced in the nitinol wire by exploiting the SMA transition temperature. One or more transition temperatures that change the shape of the nitinol can be selected just above the body temperature. Small electrical pulses can be sent along the wire to cause just enough heat increase to transition and change the shape of the wire. In at least some embodiments, the wire can cool in the blood flow after the electrical pulse to transition back to its original shape or configuration at the lower temperature below the activation temperature. The pulsing can cause the wire to move back and forth in a vibration mode. The resulting vibrations can accomplish the desired motion that creates ultrasound reflections over a greater area for a more detectable object.

Two aspects of the motion can enhance the size and noticeability of an ultrasound image pixel variation. First, the speed of the motion of the wire can be varied. For example, if the ultrasound is measured 30 times a second, the wire can be heated and cooled at an integer multiple of 1/30 second, and the resulting flickering pixels can synchronize to the image and become more visible. Other frequencies of the ultrasound and the synchronization are possible. Different integer multiples can be used in characterizing the most noticeable flicker. Second, the shape to which the wire transitions can have a profound effect on the scattering. For example, SMA coils image particularly well.

Illustrative Lateral System Embodiments

Using at least some of the principles herein for inducing lateral motion, objects can be designed to maximize the return wave intensity in the ultrasound imaging. Such objects can include but not limited to wires, such as guidewires, guidewire tips, instruments and other end effectors, and other objects sized and suitable for the particular application that are not transparent to an ultrasound wave.

FIG. 1A is a schematic diagram of an embodiment of an ultrasound system with an example of a suitable object to be detected, such as a wire, in a first state. An exemplary system 2 includes an ultrasound system 6 and an object activation subsystem 30 that can obtain images of an object 20 through a substance 4. Without limitation, the object 20 can be a wire, such as a guidewire that can used in medical procedures. The substance 4 as the medium can be body tissues or other material through which an ultrasound wave can traverse. The substance 4 will often have a passageway through which the object can travel. A passageway with the surrounding wall is shown and described in the Figures as an example herein of a substance 4 and sometimes is referenced herein as "passageway 4" with the understanding that the substance is not limited to a passageway and the invention can function in applications without a passageway.

The system 2 generally can include generally accepted components including a transducer 8 that transmits ultrasound waves into the substance 4 to different depths depending on the frequency of the ultrasound wave (and therefore the wavelength). A cross sectional width that is normal to the wave is generally the reflecting surface. If the actual width of the object is not normal to the wavefront, the projected width that accounts for the angular misalignment to the wavefront can be determined. (In the Figures, the widths "W" are illustrated from a viewpoint of a rotated plane to the direction that the transducer produces waves to illustrate the varying widths in the 2D Figures and can be conceptually rotated into the Figure to be facing the direction of the incoming waves, that is, a direction that is normal to the waves). In this embodiment, a first width W1 means the width of the object without intended activation, as viewed from a normal direction to the ultrasound wavefront. A controller 10 controls the application of power from a power supply 12, generally in energy pulses, to a transmitter/receiver switch for sending the energy pulses to the transducer 8 and for receiving reflected and/or transmitted waves from the transducer. The controller 10 can also include a processor for processing resulting waves and providing information to an output 14 of the results, generally a display for visual images.

The object activation subsystem 30 can include a controller 32 for controlling application of energy from a power supply 34 to the object 20 to activate the object as described below. In FIG. 1A, the object 20 can be at a null energy level 36, that is, at an energy level that exists without applied energy or with an amount of applied energy that does not cause the designed movement of the object. At the null energy level, the object can be at a first state having a first state position 44. The object 20 can be advanced manually, robotically, remotely, and by other methods into the substance 4.

Figure 1B:
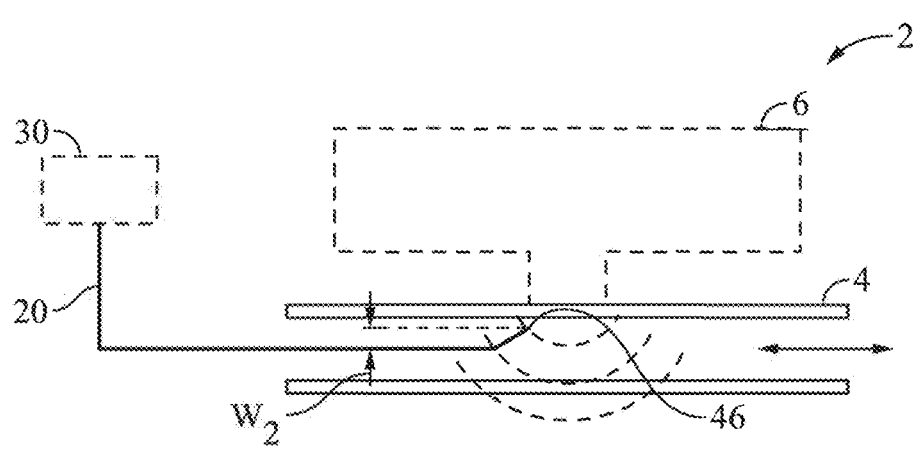
FIG. 1B is a schematic diagram of the embodiment of FIG. 1A with the object in a second state.
Figure 1C:
FIG. 1C is an illustrative pulse form for applying energy to the object of FIG. 1B.

FIG. 1B is a schematic diagram of the embodiment of FIG. 1A with the object in a second state. FIG. 1O is an illustrative pulse form for providing energy to the object. The object can be at a null energy level at the first state position where the object is not activated to the designed SMA motion. From a null energy level 36 of the object 20, the object activation subsystem 30 can apply an activation energy level 38 to the object 20 to cause deformation to a second state having a second state position 46. Energy pulses can cause the deformation at the activation energy level. Stopping or at least reducing the energy allows return of the object to a first state at the null energy level that allows the object to return to the first state position 44. The object movement occurs across an area that has a width W2 that is larger than the width W1 occupied by the object when at the null energy level. With repeated energy pulses, the object movement occurs with a plurality of cycles between the first state position 44 and the second state position 46. Ultrasound waves can encounter the object at the first state position 44 and the second state position 46, depending on the frequencies of the movement and the ultrasound waves. The ultrasound reflections from the first state position and the second state position from the movement of the object can be used to create an ultrasound image of the object at the second state that is brighter than an ultrasound image of the object at the first state. In such embodiments, the larger width W2 encompassing the movement between the first state position and second state position can become an apparent width of the object that is imaged by the ultrasound waves. Thus, the movement of the object between the first state position and the second state position can create a brighter image.

As discussed above, energy pulsing at a particular frequency can be beneficial in capturing the benefit of the object movement. When timed in relation to the ultrasound wave frequency, the larger movement of the object can be imaged. Repeated images increase an ability to detect the object more clearly.

Figure 2A:
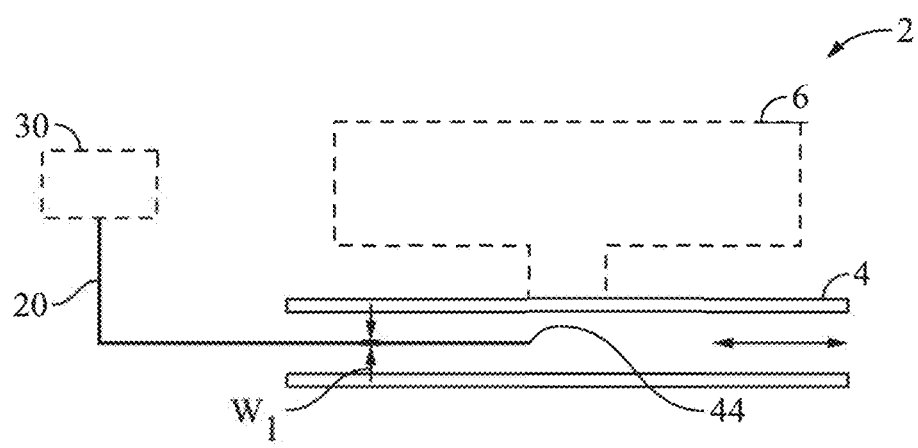
FIG. 2A is a schematic diagram of another embodiment of an ultrasound system with an exemplary object to be detected in a first state.

FIG. 2A is a schematic diagram of another embodiment of an ultrasound system with an exemplary object to be detected in a first state. In this embodiment, the functions and system are similar to the description above. However, the object 20 and the object activation system 30 varies from the embodiment of FIGS. 1A and 1B in that the wire can be made of a 2-way SMA material. A 2-way SMA material has two activation shapes of the same object 20, illustrated as a wire, at different energy levels for different temperatures. The wire can be made to move in different directions at the different temperatures. Although not shown, different portions of the wire can be made to deform at the different temperatures. Thus, the object activation system 30 can provide and control two activation energy levels. As shown, in a first state, the object 20 can be at a null energy level for a first state at a first state position 44. The width W1 is therefore the width of the object cross section facing the transducer produced ultrasound wave (that is, a direction that is normal to the wave) and may be difficult to determine by the waves from the ultrasound system 6.

Figure 2B:
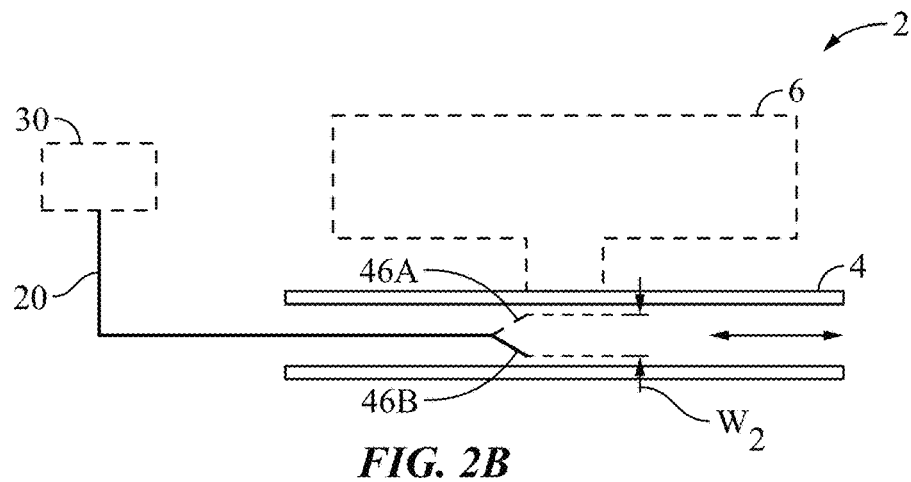
FIG. 2B is a schematic diagram of the embodiment of FIG. 2A with the object in a second state.
Figure 2C:
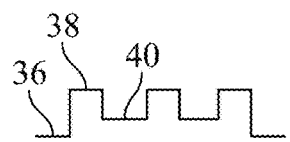
FIG. 2C is an illustrative pulse form for applying energy to the object of FIG. 2B.

FIG. 2B is a schematic diagram of the embodiment of FIG. 2A with the object in a second state. FIG. 2C is an illustrative pulse form for applying energy to the object of FIG. 2B. The object can be energized from a null energy level 36 at the first state to a first activation energy level 38 or a lower second activation energy level 40 by the object activation subsystem 30 to change to the second state. Depending on the activation energy level, the shape of the object can change from the first state in FIG. 2A to a second state resulting in either the second state position 46A or second state position 46B, shown in FIG. 2B. In at least one embodiment, alternating pulses between a first activation energy level 38 and a second activation energy level 40 can move the wire laterally in opposite directions to create an apparent width W2 that is larger than the W1 at the first state and in which the object can reflect ultrasound waves from a wider area. An ultrasound image created from reflected ultrasound waves at the second state appear brighter than an ultrasound image of the object at the first state. The applied levels of energy can vary depending on the particular SMA material.

Figure 3A:
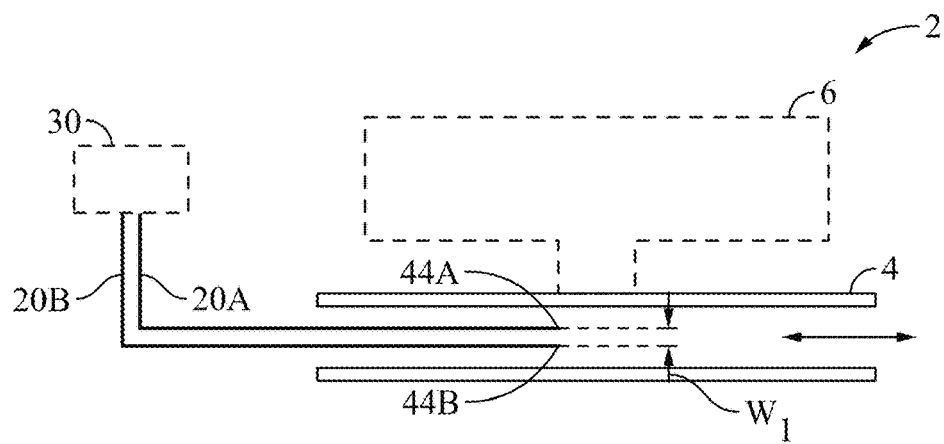
FIG. 3A is a schematic diagram of another embodiment of an ultrasound system with an exemplary object to be detected in a first state.

FIG. 3A is a schematic diagram of another embodiment of an ultrasound system with an exemplary object to be detected in a first state. In this embodiment, the functions and system are similar to the descriptions above. However, the object 20 and the object activation system 30 vary from the above embodiments in that the object 20 can be made of a plurality of wires, illustrated as two wires 20A and 20B. Each wire can have a memory shape at the same or different activation energy levels. Thus, the object activation system 30 can provide and control activation energy levels for each wire, alone or in combination with other wires. As shown, in a first state, the object 20 can be at a null energy level 36 at a first state position 44. The first width W1 is therefore a width of the object across the combined cross sections of the plurality of wires 20A and 20B in a direction that is normal to an ultrasound wave, and the object with a first width W1 may be difficult to determine by the waves from the ultrasound system 6.

Figure 3B:
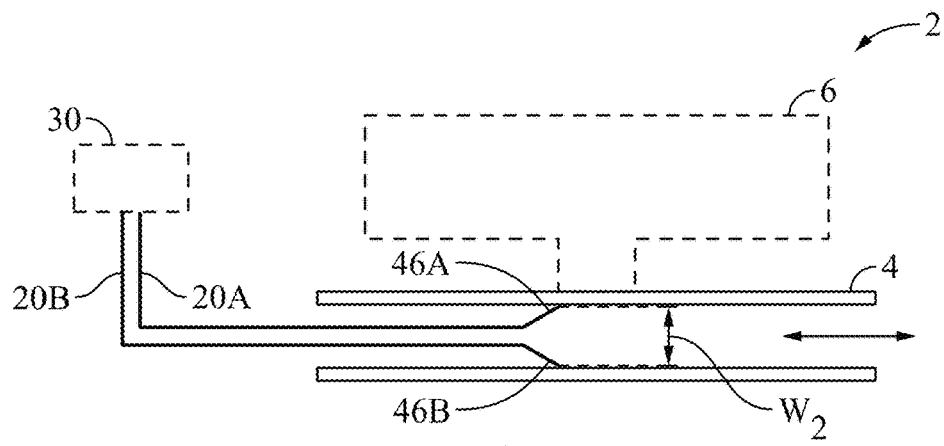
FIG. 3B is a schematic diagram of the embodiment of FIG. 3A with the object in a second state.
Figure 3C:
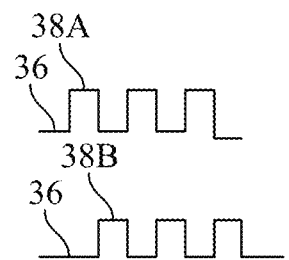
FIG. 3C is an illustrative pulse form for applying energy to the object of FIG. 3B.

FIG. 3B is a schematic diagram of the embodiment of FIG. 3A with the object in a second state. FIG. 3C is an illustrative pulse form for applying energy to the object of FIG. 3B. The object activation subsystem 30 can energize the object 20 from a null energy level 36 to an activation energy level 38 by energizing at least one of the wires 20A and 20B, such as wire 20A. With activation, the shape of the wire 20A can change from the first state in FIG. 3A to a second state having a second state position 46A shown in FIG. 3B. The object activation subsystem 30 can stop the energy to the wire 20A and energize the wire 20B from a null energy level 36 to an activation energy level 38. With activation, the shape of the wire 20B can change from the first state in FIG. 3A to a second state having a second state position 46B shown in FIG. 3B. The wires 20A and 20B can move laterally in opposite directions to increase the apparent width W2 of the object for greater ultrasound response and an increased differential in the object ultrasound images between the first and second states. Alternatively, the object activation subsystem 30 can activate both of the wires 20A and 20B simultaneously for simultaneous movement, and thus the pulse forms in FIG. 3C would be synchronized.

Figure 4A:
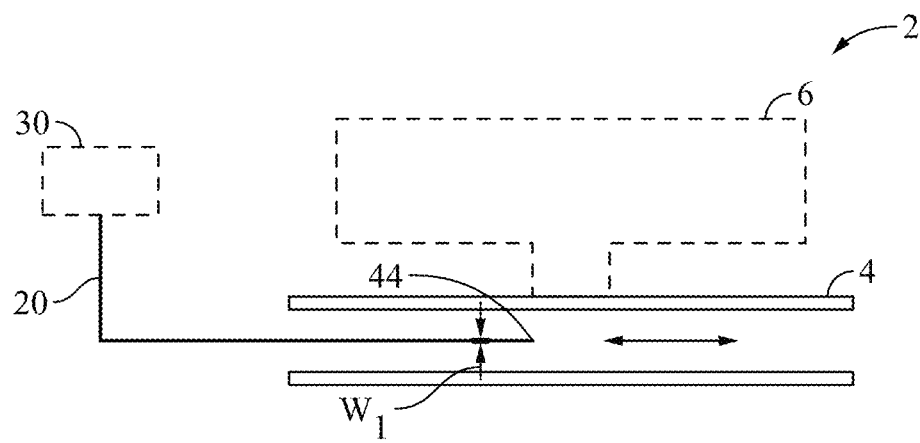
FIG. 4A is a schematic diagram of another embodiment of an ultrasound system with an exemplary object to be detected in a first state.

FIG. 4A is a schematic diagram of another embodiment of an ultrasound system with an exemplary object to be detected in a first state. This embodiment is similar to the embodiment described in FIGS. 1A and 1B. In this embodiment, the object 20 can be formed to twist into a helical coil upon activation. The object 20 can be in a first state at a null energy level having a first state position 44. As the object 20 is advanced longitudinally in the passageway 4, the ultrasound system may have difficulty locating and showing the object 20 having a first width W1 of the cross section of the wire in a normal direction to ultrasound waves.

Figure 4B:
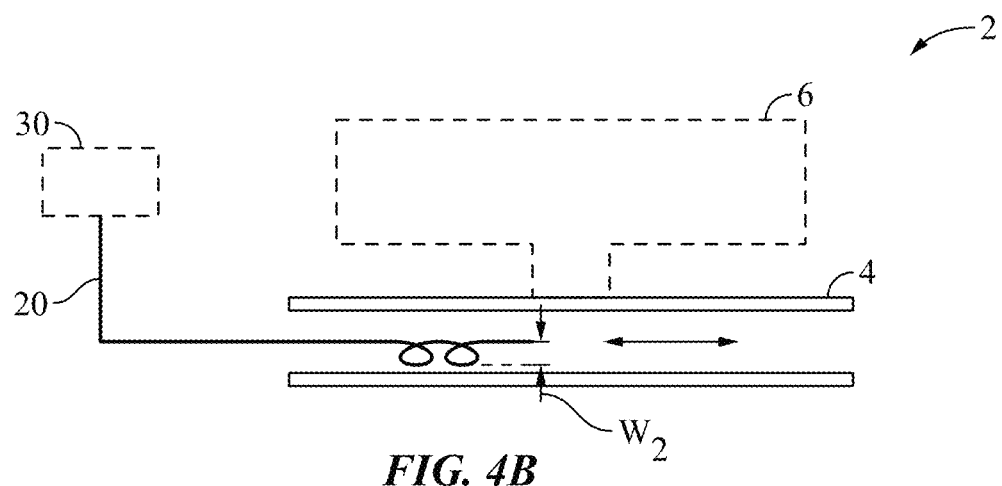
FIG. 4B is a schematic diagram of the embodiment of FIG. 4A with the object in a second state.
Figure 4C:
FIG. 4C is an illustrative pulse form for applying energy to the object of FIG. 4B.

FIG. 4B is a schematic diagram of the embodiment of FIG. 4A with the object in a second state. FIG. 4C is an illustrative pulse form for applying energy to the object of FIG. 4B. The object activation subsystem 30 can apply energy to the object, so that the object is activated into a second state. The object 20 can twist into the helical coil having a second state position 46, so that the apparent width W2 of the object shaped as a coil is more readily detected as being brighter by the ultrasound system 6.

The embodiment in FIGS. 4A-4C also illustrates that the second state can occur at one or more portions along the length of the object and is not restricted to a leading portion or leading tip of the object.

Figure 5A:
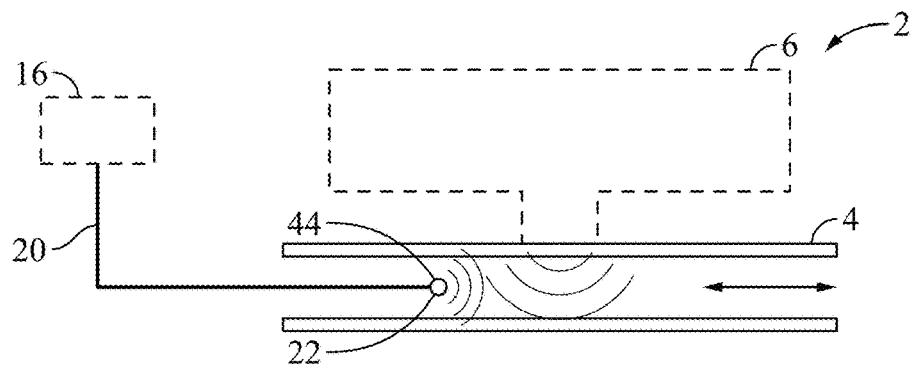
FIG. 5A is a schematic diagram of another embodiment of an ultrasound system with an exemplary object to be detected in a first state.

FIG. 5A is a schematic diagram of another embodiment of an ultrasound system with an exemplary object to be detected in a first state. This embodiment includes an object ultrasound subsystem 16 to control and operate the object 20 having a transducer 22 in a similar manner as described for the ultrasound system 6 with the transducer 8. The object 20 with the transducer is in the first state at a first state position 44 that may be distal from the transducer 8 and thus may not have sufficient energy to be sensed by the ultrasound system 6 to determine the object.

Figure 5B:
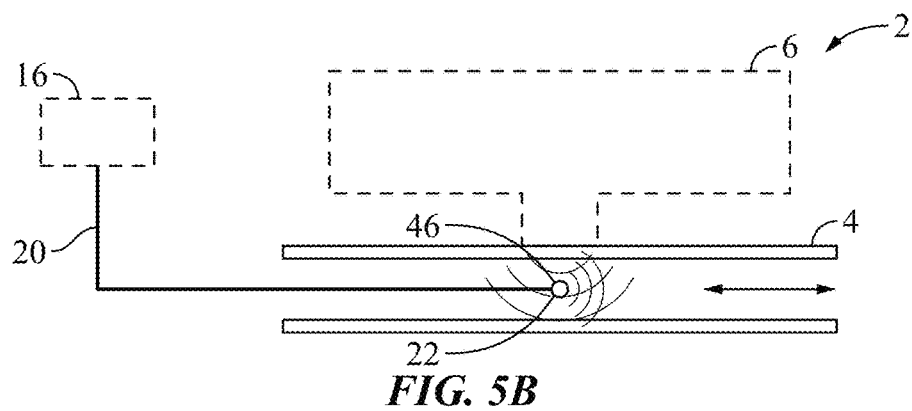
FIG. 5B is a schematic diagram of the embodiment of FIG. 5A with the object in a second state.

FIG. 5B is a schematic diagram of the embodiment of FIG. 5A with the object in a second state. As the object transducer 22 moves longitudinally in the passageway into proximity with the ultrasound system 6, ultrasound waves from the object transducer 22 have sufficient energy to be sensed by the ultrasound system 6 in a second state at a second state position 46. The transducer 22 sound waves are more readily received by the ultrasound system 6 as an incoming beacon signal. The movement from the first state position to the second state position and attendant emission of the ultrasound waves from the object transducer 22 at the second state yields a brighter ultrasound image of the object from the ultrasound system 6 compared to an ultrasound image of the object at the first state.

Longitudinal Motion

Longitudinal motion of the guidewire can cause dynamic speckle variations in similar ways as the lateral movements. The detection of the object can be independent of activation energy applied to the object. The ultrasound system can detect structure of the surrounding tissues, bones, and so forth, but small objects can show as scattered speckles and be indeterminate. However, by comparing speckle output at different times of movement between a first state and a second state of the object, the dynamic speckle can be used to detect small objects, where the speckle pattern is uniform prior to the object entering a field of view of the ultrasound system.

Illustrative Longitudinal System Embodiments

Figure 6A:
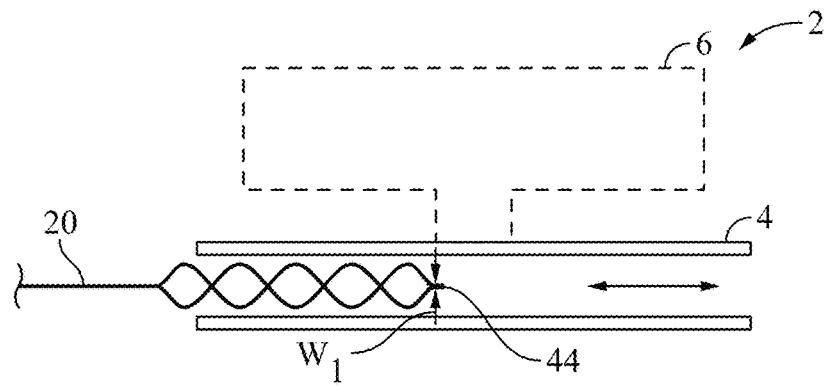
FIG. 6A is a schematic diagram of another embodiment of an ultrasound system with an exemplary object to be detected in a first state.

FIG. 6A is a schematic diagram of another embodiment of an ultrasound system with an exemplary object to be detected in a first state. In this embodiment, the detection of the object 20 is independent of activation energy applied to the object. The object 20 can include a variable cross sectional shape along a length of the object. The wires could be twisted at a set period down a length of the wire. The cross section would appear to vary in the ultrasound imaging with the longitudinal motion (forward or backward) of the object, and the reflection would also vary. As shown in FIG. 6A, the object in a first state in a first state position 44 presents a narrow cross section width W1 under the ultrasound system 6 for detection but may be difficult to detect at that size.

Figure 6B:
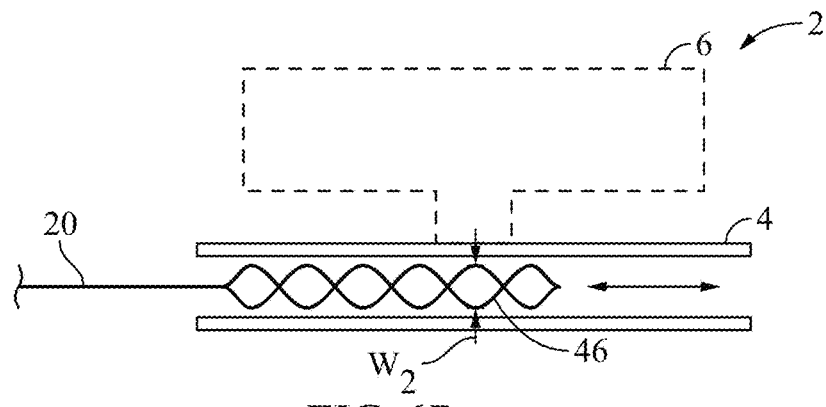
FIG. 6B is a schematic diagram of the embodiment of FIG. 6A with the object in a second state.

FIG. 6B is a schematic diagram of the embodiment of FIG. 6A with the object in a second state. As the object 20 longitudinally moves to a second state with a second state position 46 in the passageway 4, the cross section of the object increases. At the second state position 46, a greater width W2 is presented to the ultrasound system 6 that differs from the first width W1 at the first state position 44 and is more readily detected in an ultrasound image at the second state.

Figure 7A:
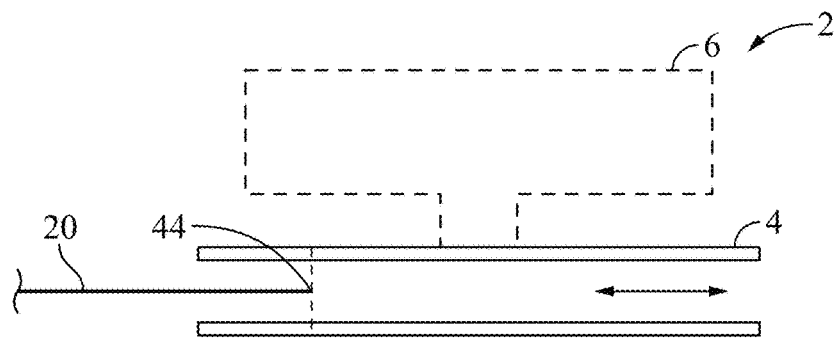
FIG. 7A is a schematic diagram of another embodiment of an ultrasound system with an exemplary object to be detected in a first state.

FIG. 7A is a schematic diagram of another embodiment of an ultrasound system with an exemplary object to be detected in a first state. In this embodiment, the detection of the object 20 is independent of activation energy applied to the object. The object 20 can stay the same width. Before the object 20 moves longitudinally and enters a field of view of the transducer in a first state at first state position 44, the speckle can be uniform. If the object is in the field of view but stationary in a first state at a first state position, the speckle can be constant. In either case of potential first states and first state positions, the speckle may not provide sufficient information to detect or characterize the object.

Figure 7B:
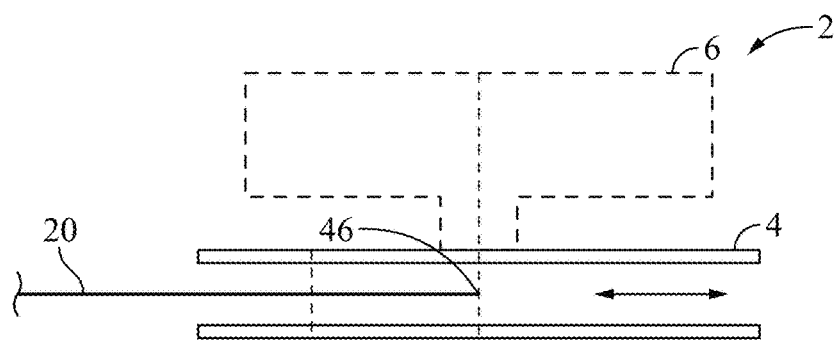
FIG. 7B is a schematic diagram of the embodiment of FIG. 7A with the object in a second state.

FIG. 7B is a schematic diagram of the embodiment of FIG. 7A with the object in a second state. As the object 20 moves into view of the ultrasound system 6 at a second state with a second state position 46, a comparison between progressive images can show the speckle changes from otherwise indeterminate speckle. As the object leading portion, such as a wire tip, is moved longitudinally and approaches the ultrasound transducer, flicker from speckle scattering of secondary lobes can cause potentially noticeable effects on the ultrasound output. Finally, once the tip is in the field of view, a different speckle pattern will be generated. This dynamic speckle patterning can be detected and characterized, and thus used to locate the object. As the object continues to advance longitudinally, subsequent analyses of progressive images can detect speckle caused by the object and location and other characterization aspects.

Reciprocal forward and backward longitudinal motion of the object 20 enhances the differential in reflected ultrasound waves and increases the brightness of ultrasound images created therefrom.

Figure 8A:
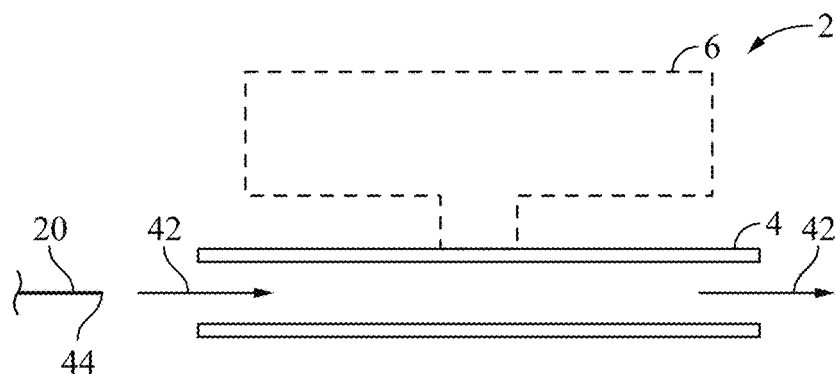
FIG. 8A is a schematic diagram of another embodiment of an ultrasound system with an exemplary object to be detected in a first state.

FIG. 8A is a schematic diagram of another embodiment of an ultrasound system with an exemplary object to be detected in a first state. In this embodiment, an object 20 can be detected by using a Doppler ultrasound in the ultrasound system 6. A Doppler ultrasound is a test that uses ultrasound waves to measure the amount of blood or other fluid flow 42 generally through passageways, such as arteries and veins. In this embodiment, the object can be remote to the transducer region of the ultrasound system 6 in a first state at a first state position 44. The fluid flow 42 through the passage 4 can be detected in the first state without the object being in proximity to the view of the ultrasound system 6 that would affect flow. An ultrasound image at the first state may not reveal the object, since there is no discernible effect on the fluid flow 42.

Figure 8B:
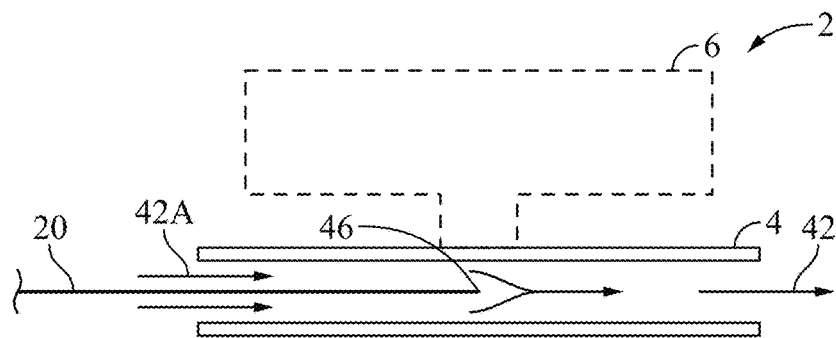
FIG. 8B is a schematic diagram of the embodiment of FIG. 8A with the object in a second state.

FIG. 8B is a schematic diagram of the embodiment of FIG. 8A with the object in a second state. In the second state, the object 20 can be advanced into view of the ultrasound system 6 at a second position 46 with a fluid flow 42A that is split into a flow around the object 20. The reduction in flow area by the cross sectional areas of the object in the flow path causes an increase in flow rate. The flow rapidly converges after flowing over the tip where the flow area is no longer restricted by the object. With the full flow area, the fluid slows down. The difference from movement of the object between first state position 44 and second state position 46 leads to the Doppler ultrasound determination of the presence of the tip (or other leading edge of an object 20 as appropriate).

Because the substance 4, such as the passageway, generally has a constant position, the changes in the speckle can indicate the location and movement of the object 20, even though the object 20 may not be determinate on individual images. Such determination may not be readily accomplished by human eye visual inspection. The invention contemplates a scanner to scan a digital map of a plurality of digital images or other input device and digitally compares values of different portions of the map such as comparing portions by pixels or groups of pixels in the same map coordinates between the progressive images. Differences, and particularly progressive differences, that show a path of the changing speckle provide greater probability of the detection and characterization of the object 20. This aspect can apply to any of the embodiments described herein as examples and more generally to the invention.

In at least one embodiment, the system can include a robotically controlled, surgical guidewire for the treatment of neurovascular conditions, such as stroke and cancer. The system can also include multiple sensors such as pressure, acoustic, electrical, chemical, and optical sensors, within a tip coupled to the guidewire. For example, pressure sensors can be used to detect a clot or tumor, while electrical sensors can cause an electrically induced chemical reaction to lyse clots and destroy tumors.

Figure 9A:
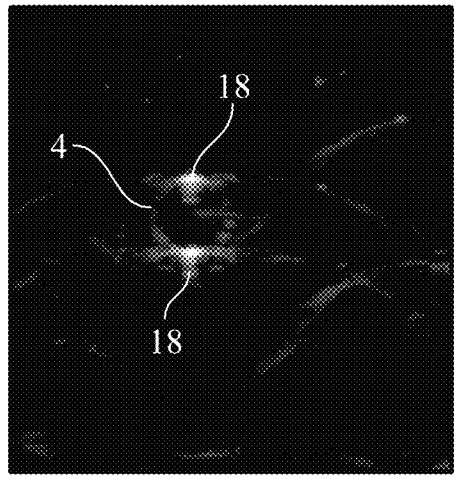
FIG. 9A is an illustrative ultrasound image from an end view showing a passageway in a substance without an object to approximate an ultrasound response in a body tissue.
Figure 9B:
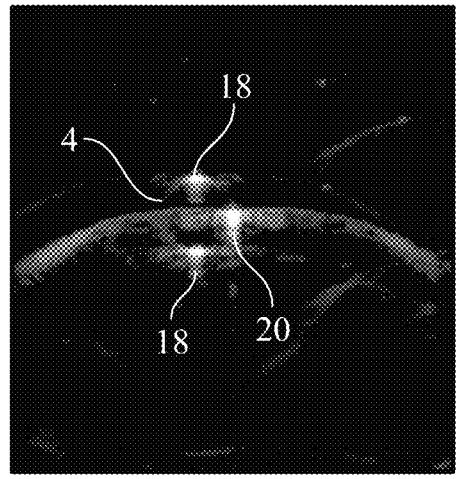
FIG. 9B is the ultrasound image of FIG. 9A at a different time with additional speckle showing an object that has entered into the ultrasound system range.
Figure 9C:
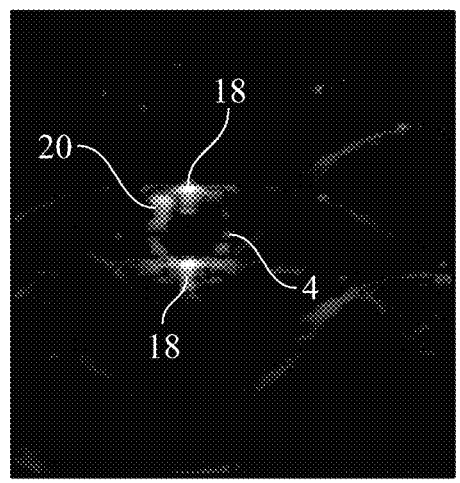
FIG. 9C is an ultrasound image of FIG. 9A at another different time with speckle showing an object in a different location of the passageway compared to FIG. 9B.

FIG. 9A is an illustrative ultrasound image from an end view showing a passageway in a substance without an object to approximate an ultrasound response in a body tissue. FIG. 9B is the ultrasound image of FIG. 9A at a different time with additional speckle showing an object that has entered into the ultrasound system range. FIG. 9C is an ultrasound image of FIG. 9A at another different time with speckle showing an object in a different location of the passageway compared to FIG. 9B. The concept tests were made in a primarily gelatin/water mix with a passageway formed therein to simulate a body tissue substance 4. An object 20, and in these tests specifically a guidewire, was inserted into the substance with an ultrasound system described above positioned to record the object 20 as it was advanced into the view of the ultrasound system. The illustrative embodiment used for these tests corresponds generally to the system and method discussed in FIGS. 7A and 7B. The passageway is shown as an end view. The image in FIG. 9A illustrates speckle of reflections 18 from the substance independent of an object. The object may be too remote to ultrasound sensing in a first state or too small in the first state to be detectable. Internal reflections 18 as speckle are shown at a top and bottom (that is, a 12 o'clock and 6 o'clock position) of the passageway in the orientation of the figures. Because the internal reflections 12 o'clock and 6 o'clock position stay uniform in FIGS. 9A, 9B, and 9C, then an analysis of any differences in the images as the object is advanced into viewing range will likely enable the object detection and the differences can be used to characterize the object. In FIG. 9B, the difference in speckle from FIG. 9A is a group of concentrated speckle at a 3 o'clock position adjacent an internal wall of the passageway. In FIG. 9C, the difference in speckle from FIGS. 9A and 9B is a group of concentrated speckle at an 11 o'clock position adjacent the passageway wall.

Remarkably, all of these images were produced using a small, subwavelength object of 100 µm wire inside a one-quarter inch (0.6 cm) passageway with a frequency of 7.5 MHz. The wavelength of a 7.5 MHz is about 200 µm in the substance surrounding the wire. The 100 µm cross section of the wire is about one-half of the ultrasound wavelength and yet the ultrasound system was able to detect the wire. The test was also performed with larger wires of 125, 150, and 250 µm cross sections and predictably did at least as well as the smaller 100 µm cross section wire.

In summary, the system can be designed to detect ultrasound reflections from otherwise indistinguishable objects, including the use of speckle patterns, or use Doppler flows to locate even a subwavelength object.

Further, the principles described herein can be applied to endovascular navigation as the passageways and to other passageways and other parts of a body, as well as to resolution in other imaging modalities. The principles can be applied to other substances, even nonorganic substances, that are conducive to ultrasound wave detection. Among various advantages, improved accuracy can improve navigational speed while minimizing or eliminating damaging other tissue.

Other and further embodiments utilizing one or more aspects of the inventions described above can be devised without departing from the disclosed invention as defined in the claims. For example, other embodiments can include other subwavelength objects, non-uniform cross sections, variations in material between tips and guidewire, variations in methods of causing lateral and longitudinal motion, and variations other than those specifically disclosed above within the scope of the claims.

The invention has been described in the context of preferred and other embodiments and not every embodiment of the invention has been described. Obvious modifications and alterations to the described embodiments are available to those of ordinary skill in the art. The disclosed and undisclosed embodiments are not intended to limit or restrict the scope or applicability of the invention conceived of by the Applicant, but rather, in conformity with the patent laws, Applicant intends to protect fully all such modifications and improvements that come within the scope of the following claims.

What is claimed is:

1. A system for detecting one or more objects with ultrasound imaging technology that images by producing ultrasound waves from an ultrasound system, the ultrasound waves having a frequency with a corresponding ultrasound wavelength, comprising:
    an object having a first state at a first state position that is configured to be exposed to a wavefront of the ultrasound waves and a second state by a movement of the object to a second state position that is different from the first state position, wherein the ultrasound waves reflect from the first state position to create a first speckle pattern and the second state position to create a second speckle pattern that is different than the first speckle pattern, wherein a difference between the first speckle pattern and the second speckle pattern indicates a location of the object.

2. The system of claim 1, wherein the movement of the object further comprises movement from the second position back to the first position to create repeated movement at a frequency between the first position and the second position.

3. The system of claim 2, wherein the movement of the object at the frequency is synchronized with the ultrasound frequency to create an ultrasound image with the object at the first state position and the second state position.

4. The system of claim 1, wherein the object has at least one cross sectional dimension that is smaller than the ultrasound wavelength in a substance in which the object is to be detected.

5. The system of claim 1, wherein the system further comprises a controller configured to control energy from a power supply to cause vibration of the object at least when the object is exposed to the ultrasound waves.

6. The system of claim 5, wherein the object comprises a shape memory material configured to deform at a first temperature at one or more activation energy levels.

7. The system of claim 5, wherein the object comprises a shape memory material configured to deform at a first temperature at a first activation energy level and a second temperature at a second activation energy level.

8. The system of claim 7, wherein the object is configured to deform in a first direction at the first activation energy level and deform in a second direction that is different from the first direction.

9. The system of claim 8, wherein the second state comprises a plurality of second state positions.

10. The system of claim 5, wherein the object comprises a plurality of wires coupled to the system and the plurality of wires configured to be activated by the system.

11. The system of claim 10, wherein at least a first wire of the object is configured to deform in a first direction and at least a second wire of the object is configured to deform in a second direction that is different from the first direction.

12. The system of claim 5, wherein the object is configured to deform into a helical coil upon activation by the system.

13. The system of claim 5, wherein the object comprises an object ultrasound subsystem configured to emit ultrasound waves and wherein the object at the first state is at the first state position distant from the ultrasound system, and wherein the movement of the object to the second state at the second state position is in proximity to the ultrasound system and allows the ultrasound system to sense the ultrasound waves from the object ultrasound subsystem and create a different ultrasound image of the object at the second state position from an ultrasound image at the first state position.

14. The system of claim 1, wherein the object is at the first state at the first state position and the object is longitudinally moved to establish the second state at the second state position.

15. A method of detecting one or more objects using ultrasound imaging technology that images by producing from an ultrasound system an ultrasound wave having a frequency with a corresponding ultrasound wavelength, comprising:

placing an object capable of at least partially reflecting ultrasound waves into a substance that at least partially conducts ultrasound waves, the object having a first state at a first state position;

moving the object to a second state at a second state position that is different than the first state position;

allowing ultrasound waves from the ultrasound system to be reflected from the object at the first state position and the second state position; and creating a first speckle pattern at the first state position and a second speckle pattern at the second state position, wherein a difference between first speckle pattern and the second speckle pattern determines a location of the object.

16. The method of claim 15, wherein the step of moving the object comprises applying pulsed energy to the object.

17. The method of claim 16, wherein the pulsed energy is applied at a frequency that is synchronized with the ultrasound frequency.

18. The method of claim 16, wherein the object comprises a shape memory alloy and further comprising deforming the object with the pulsed energy.

19. The method of 16, wherein the object comprises a shape memory alloy and further comprising deforming the object in a plurality of directions with the pulsed energy.

20. The method of claim 15, wherein the step of moving the object comprises moving the object longitudinally between the first state position and the second state position.

* * * * *